US00PP10291P

United States Patent [19]

Cooper et al.

[11] Patent Number: Plant 10,291

[45] Date of Patent: Mar. 24, 1998

[54] FUJI APPLE TREE: 'FUJI COMPACT T.A.C. #114'

[75] Inventors: Calvin L. Cooper, Brewster; Wilbur R. Perkins, Bridgeport, both of Wash.

[73] Assignee: T.A.C. Tree Co., Orondo, Wash.

[21] Appl. No.: 618,257

[22] Filed: Mar. 18, 1996

[51] Int. Cl.[6] ..... A01H 5/00

[52] U.S. Cl. ..... Plt./34.1

[58] Field of Search ..... Plt./84.1

[56] References Cited

U.S. PATENT DOCUMENTS

P.P. 9,508 4/1996 Lynd ..... Plt./34.1

*Primary Examiner*—James R. Feyrer

*Attorney, Agent, or Firm*—Klarquist Sparkman Campbell Leigh & Whinston

[57] ABSTRACT

The 'Fuji Compact T.A.C. #114' strain of Fuji Apple Tree (*Malus domestica*) characterized by the significant compactness of its growth habit and the unique color and "finish" characteristics of its fruit, which is similar in all respects to fruit from its parent 'Fuji Apple Tree: T.A.C. #114' (U.S. Plant Pat. No. 8,032).

1 Drawing Sheet

This invention relates to a new and distinct variety of apple tree, specifically to the Fuji Apple Tree variety denominated the 'Fuji Compact T.A.C. #114' Strain (*Malus domestica*).

The new variety of apple tree was discovered in the year 1991, in the cultivated nursery of Wilbur R. Perkins, located approximately two miles northeast of State Highway 17 on Jack Wells Road at Bridgeport, Wash. This Strain derived from scion wood cut from the original Fuji Apple Tree: T.A.C. #114 Strain, (U.S. Plant Pat. No. 8,032).

Figure 1:
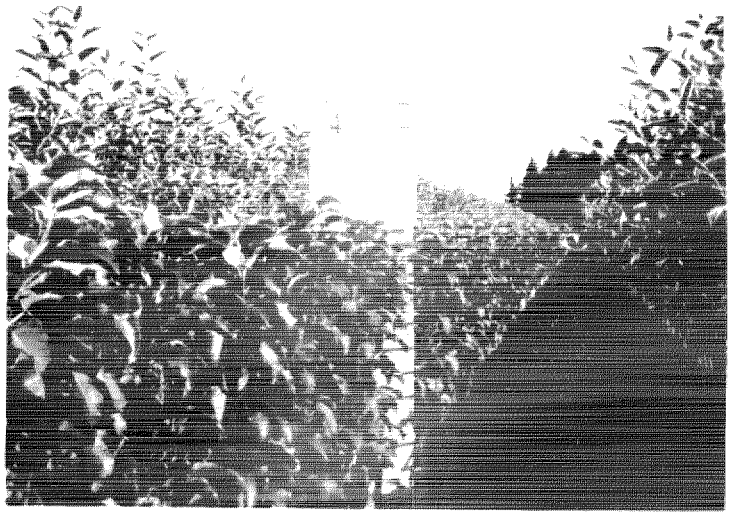

The tree was conspicuous because of its markedly different growth habit (FIG. 1). It was approximately 40–60% of the size of its parent. In U.S. Plant Pat. No. 8,032 the new Fuji apple tree variety which is the subject matter of that patent (T.A.C. #114), is characterized as being a compact variety when compared to 'Standard Fuji'. The subject Fuji apple tree, denominated herein the 'Fuji Compact T.A.C. #114' strain is significantly more compact than its parent (Fuji Apple Tree 'T.A.C. #114') (Table 1). In terms of growth habit, the subject Fuji apple tree is very similar to the 'Fuji-Spike' Apple Tree (U.S. Plant Pat. No. 9,508) (Table 1). Trees of 'Fuji Compact T.A.C. #114' and 'Fuji-Spike', of the same age, growing in adjacent rows, on the same rootstock, and under the same cultural conditons, at East Wenatchee, Wash., have been observed to appear identical in terms of branching habit, openness, size, foliage characteristics, color of bark, color of leaves, color and appearance of buds (spur and leaf).

The subject, 'Fuji Compact T.A.C. #114' differs from the 'Fuji-Spike' Apple Tree in that: (1) it tends to have slightly more spurs, dards and short shoots per linear meter of branch length (Table 1), and (2) it tends to have slightly shorter internodes and "thicker" limb diameters (Table 1 and FIG. 2). Also, fruits from 'Fuji Compact T.A.C. #114' (like its parent strain 'T.A.C. #114'), and in comparision to the description of fruit of 'Fuji-Spike' trees as set forth in U.S. Plant Pat. No. 9,508, (a) are a more brilliant tone of red color; (b) had red color comprised of a narrow, red on red stripe pattern, rather than a uniform coloration or blush; and (c) had red coloration covering from 80 to 95% of the total apple surface. By contrast, according to U.S. Plant Pat. No. 9,508, the 'Fuji-Spike' Apple Tree produces fruit that is similar to 'Yataka' (U.S. Plant Pat. No. 7,001) and the 'Fuji' variety, both of which produce fruit quite similar, if not identical, to 'Fuji-Spike'.

While the magnitude of the growth habit differences between 'Fuji Compact T.A.C. #114' and 'Fuji-Spike' are small (Table 1), the compact growth habit, precocious nature in combination with the high fruit color of this strain does offer considerable advantage over other available 'Fuji' strains in modern orchard management systems.

The color tone, patterns, and the amount of the fruit surface covered with "Red Color" (Table 1) are of considerable horticultural and commercial significance. The fruits of 'Fuji-Spike' (being similar to 'Yataka' and 'Fuji', according to U.S. Plant Pat. No. 9,508) would have significantly less "Red Color", in terms of the tone, and the percentage of the fruit surface developing red color, than the subject strain ('Fuji Compact T.A.C. #114'). The combination of the spur-type, semi-dwarf growth habit, and the high level of "Red Color" (Table 1 and U.S. Plant Pat No. 8,032) result in the subject strain being a unique selection.

TABLE 1

| CULTIVAR | Internodal Length (mm) | Spurs/Linear Meter of Branch* | Fruit Color % Surface Red |
|---|---|---|---|
| 'B.C. Redsport II' | 22 | 17 | 45 |
| Nagafu #6 | 21 | 19 | 60 |
| Standard Fuji*** | 22 | 17 | 45 |
| Yataka | 23 | 18 | 40 |
| 'Fuji-Spike' | 14 | 34 | 40–45** |
| 'T.A.C. #114' | 16 | 28 | 85 |
| 'Compact T.A.C. #114' | 12 | 39 | 85 |

*Includes spurs, dards and shoots.

**From U.S. Plant Pat. No. 9,508 description that 'Fuji-Spike' is similar to 'Standard Fuji' and 'Yataka'.

***Observations from 'Standard Fuji' trees growing in an adjacent orchard.

The other characteristics of the tree are identical with those of the parent tree, Fuji T.A.C. #114 strain. Thus the tree is indistinguishable from the parent with respect to its leaves, bark, flowers, and other physically sensible characteristics except as noted above. The fruit appears identical with respect to size, color finish, maturity, texture and flavor.

The subject tree, 'Fuji Compact T.A.C. #114' has been propagated through three generations. All of the characteristics noted above have been demonstrated to be stable and persistent from generation to generation (study made by asexual reproduction of trees).

FIG. 1 is a view illustrating the more compact growth habit of 'Fuji Compact T.A.C. #114' as compared with the parent tree, Fuji T.A.C. #114, grown in adjacent nursery rows under the same conditions. 'Fuji Compact T.A.C. #114' is shown as the intermediate row, between two rows of the parent tree, one on each side.

Figure 2:
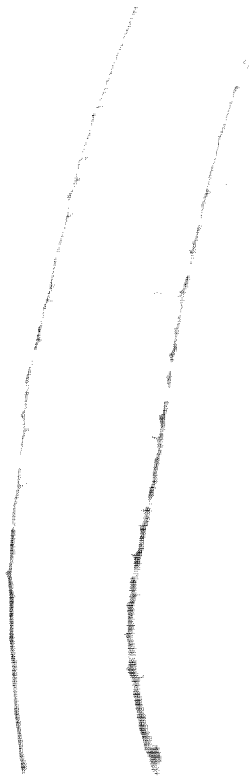

FIG. 2 is a comparison of spur and shoot density of Fuji T.A.C. #114, the parent tree, on the left with the presently described sport, 'Fuji Compact T.A.C. #114' on the right. This figure illustrates the relative internodal length and spur densities. In both cases the leaves were removed at the base of the leaf blade, leaving the petiole attached.

A more detailed botanical description of our new apple variety and of its compact growth habit and highly colored fruit follows.

BOTANICAL DESCRIPTION

Parentage: A whole tree sport of T.A.C. #114 derived from nursery stock budded in August of 1990.

Location of parent: Orchard of Calvin L. Cooper; Brewster, Wash., U.S.A.

Date of discovery: Oct. 14, 1994.

*Tree.*—Compact, spreading, highly spurred, wide limb angles, productive.

*Trunk.*—Stocky, smooth, gray green to light brown slight taper.

*Branches.*—Spreading, wide angles, thick medium density branches abundant from leaf axial buds, spurs profuse, dards abundant.

*Internodes.*—Average internode distance equals 12 mm vs 16 mm for T.A.C. #114, 22 mm for Summerland Redsport #2, and 14 mm for 'Fuji-Spike'. Yataka (U.S. Plant Pat No. 7,001) is reported to be the same as standard Fuji.

*Spurs.*—Abundant (39 per meter) more if summer pruned) (See Table 1), ¾" long, thick (7–8 mm), strong, large primary leaves.

*Leaves (primary).*—Broad, dark green, thick, glossy on upper surface; moderately pubescent lower surface. Length: 85 to 90 mm. Width: 55 to 60 mm. Petiole: Short (15 to 18 mm), thin (1.5 to 1.7 mm), pubescent. Margins: Serrate, tip to base of blade. Tip: Sharply pointed. Bracts: Prominent, borne in pairs, opposite, narrow pointed, borne 3 to 4 mm from abscission zone.

*Leaves (secondary).*—Oval, thick, dark green upper surface, moderately pubescent lower surface. Length: 55 to 60 mm. Width: 40 to 45 mm. Margins: Slightly serrate. Tip: Slightly rounded. Petiole: Long (25 to 30 mm), thin (1 to 1.5 mm) moderately pubescent. Bracts: Obscure, borne in pairs, opposite, hairlike, pointed, borne 1 to 2 mm from abscission zone.

*Flowers.*—Mid-season (April 28–30 at Brewster, Wash., extended bloom period, 3 to 4 days after 'Red Delicious'). Size: Medium. Color: White slightly pink at petal base. Stamen: Single row, anthers fleshy, yellow, turning dark brown with pollen shed. Pistil: Stigmas broad, flat at top, rounded at base; styles medium long, fused at base. Sepals: Medium size, pubescent fleshy at base.

*Fruit.*—Maturity when described — eating ripe after 60 days cold storage.

*Size.*—Medium (75 mm) to large (100 mm).

*Form.*—Oval, slightly flattened at stem and calyx ends.

*Cavity.*—Round, narrow, deep: apex acuminate, breadth 25 mm, depth 15 mm.

*Stem.*—Medium short 18–20 mm, moderately thin (1.5 to 2 mm), moderately pubescent abscission zone enlarged.

*Skin.*—Smooth, glossy, red (5R 4/12)* on red (5R 5/13)* and yellow (Plate XVI, Color No. 21', Tone b)** striped. Red most prominent toward shoulder, thinning toward calyx, lenticles widely scattered, small. Red color covers 80 to 95 percent of the entire fruit surface (vs. 40–45% for 'Fuji-Spike' (based upon description in U.S. Plant Pat. No. 9,508), 'Yataka', and 'Fuji'.

*Flesh.*—Creamy white, turning pale yellow with advanced maturity, juicy, sweet, smooth, tender, crisp, very fine texture.

*Aroma.*—Distinct, sprightly, moderately strong.

*Core.*—Sharply oval, bundle area medium, bundles — prominent.

*Basin.*—Smooth, shallow, rounded.

*Calyx.*—Lobes absent, sepals small, clasping, inconspicuous.

*Seed.*—Medium size (6 to 7 mm long, 4 to 5 mm wide), brown, sharp at embryo end, rounded distally.

*Maturity date.*—October 5 at Brewster, Wash.

Use: Fresh, dessert.

*Nickerson Color Fan — in: *System of Color Notation*; Munsell, A.H. (Brigham Young University Library QC 494.3 M85X)

***Ridgeway Color Standards & Nomenclature*: in: *Color; Universal Language and Dictionary of Names*; Lowe, K. (Brigham Young University Library QC 494.3 K44X)

We claim:

1. A new and distinct cultivar of Fuji apple tree, as illustrated and described.

* * * * *